(12) United States Patent
Li et al.

(10) Patent No.: US 11,937,961 B2
(45) Date of Patent: Mar. 26, 2024

(54) UNIVERSAL POSITIONING SYSTEM FOR X-RAY IMAGING SYSTEM

(71) Applicant: GE Precision Healthcare LLC, Wauwatosa, WI (US)

(72) Inventors: Yu Qing Li, Beijing (CN); Gireesha Chinthamani Rao, Pewaukee, WI (US); Chunyu Wang, Beijing (CN); Fusheng Li, Beijing (CN); Qingtao Wang, Beijing (CN); Feng Xu, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 114 days.

(21) Appl. No.: 17/534,529

(22) Filed: Nov. 24, 2021

(65) Prior Publication Data
US 2023/0157656 A1    May 25, 2023

(51) Int. Cl.
*A61B 6/00* (2006.01)
*A61B 6/04* (2006.01)

(52) U.S. Cl.
CPC .......... *A61B 6/4476* (2013.01); *A61B 6/0407* (2013.01); *A61B 6/4464* (2013.01); *A61B 6/548* (2013.01); *A61B 6/56* (2013.01)

(58) Field of Classification Search
CPC ..................................................... A61B 6/587
See application file for complete search history.

(56) References Cited

U.S. PATENT DOCUMENTS

| 8,591,107 B2 | 11/2013 | Peters |
| 8,727,618 B2 | 5/2014 | Maschke et al. |
| 9,089,309 B2 | 7/2015 | Bouvier |
| 2015/0124939 A1* | 5/2015 | Ahn ..................... A61B 6/4452 378/167 |

FOREIGN PATENT DOCUMENTS

| CN | 101828926 B | 10/2012 |
| CN | 208973878 U | 6/2019 |
| CN | 112770687 A | 5/2021 |
| JP | 2005131001 A | 5/2005 |
| JP | WO2017029690 A1 | 5/2018 |

* cited by examiner

*Primary Examiner* — Dani Fox
(74) *Attorney, Agent, or Firm* — Boyle Fredrickson, S.C.

(57) ABSTRACT

An X-ray system with a universal positioning system includes a multiple degree of freedom overhead support system mounted within a location for the X-ray system, a first imaging device on the overhead support system, a multiple degree of freedom wall stand disposed within the location for the X-ray system, the wall stand comprising a motive module and a number of moveable members operably connected to the motive module that can be operated by the motive module to move the wall stand over a floor of the location, a second imaging device mounted to the wall stand, a table disposed within the location for the X-ray system, including a base disposed on the floor of the location and a support surface secured at one end to the base, and a workstation including a processing unit configured to send control signals to and to receive data signals from the universal positioning system.

18 Claims, 11 Drawing Sheets

UNIVERSAL POSITIONING SYSTEM FOR X-RAY IMAGING SYSTEM

FIELD OF THE DISCLOSURE

The present disclosure relates to X-ray systems, and more particularly to X-ray systems adapted to accommodate various patient positions.

BACKGROUND OF THE DISCLOSURE

A number of X-ray imaging systems of various designs are known and are presently in use. Such systems are generally based upon generation of X-rays that are directed toward a subject of interest. The X-rays traverse the subject and impinge on a detector, for example, a film, an imaging receptor, or a portable cassette. The detector detects the X-rays, which are attenuated, scattered or absorbed by the intervening structures of the subject. In medical imaging contexts, for example, such systems may be used to visualize the internal structures, tissues and organs of a subject for the purpose screening or diagnosing ailments.

X-ray systems may be fixed or mobile. Fixed radiography systems generally utilize an X-ray source moveably mounted to ceiling in the area in which the X-rays are to be obtained. In one prior art configuration, the radiography system is an overhead tube support X-ray system 100 is shown in FIG. 1. The overhead tube support typically includes a column 105 to which the X-ray source 110 is attached, coupled to an overhead rectangular bridge 115 that travels along a system of rails or tubes 120 oriented perpendicular to the bridge 115. A transport mechanism 125 coupled to the bridge 115 operates to move the column 105 along a longitudinal horizontal axis, while the rail system 120 allows the bridge 115 to travel along a lateral horizontal axis in the same plane. The rail system 120 typically includes a front rail 120*a*, a rear rail 120*b*, and a cable drape rail (not shown) mounted to a ceiling of a room or suite housing the fixed radiography system. In some installations, the overhead tube support system 100 may be mounted to a system of struts which are fixed to the ceiling. to enable the X-ray source 110 to be oriented with respect to a fixed table 130 or fixed wall stand 135 that hold a detector 140 thereon in order to obtain desired images of the patient 145 position on or adjacent thereto.

However, the components of the overhead tube support system 100 can be expensive to produce and install. Further, positioning the X-ray source over a patient's anatomical features from a parked position of the overhead tube support system 100 may be time consuming because of the longitudinal and lateral distances being traversed and the fixed speeds of motors used to drive the overhead tube support components. Furthermore, the overhead tube support system has a limited number of degrees of freedom, making imaging some aspects of a patient's anatomy difficult.

An alternative to the overhead tube support of FIG. 1 is a fixed robotic arm X-ray system 200 shown in FIG. 2 and disclosed in U.S. Pat. No. 10,743,827, entitled Robotic Arm With X-ray Source, which is expressly incorporated herein by reference in its entirety for all purposes, have been developed. The fixed X-ray system 200 includes a robotic arm 202, a work station 204, a fixed table 206, a fixed wall stand 208, and a detector 210 that is positionable within one of the table 206 or the wall stand 208. The robotic arm 202 may be mounted to a wall or floor or a ceiling 212 of a radiography suite in order to enable an X-ray source 214 disposed on the end of the robotic arm 202 opposite the ceiling 212 to be oriented with regard to the detector 210 to produce an X-ray image of the desired portion of the patient 205 positioned directly in front of the detector 210.

The use of the robotic arm 202 provides a significant enhancement to the degrees of freedom capable for movement of the X-ray source 214 in order to properly position the X-ray source 214 in alignment with the detector 210 disposed on the table 206 or the wall stand 208. The table 206 may include a bucky 216 or other device for holding a detector 210 and can be motorized for rotational and vertical movement. For example, the work station 204 may operate the table 206 to locate a patient 205 in a particular position or orientation with respect to the X-ray source 214 during a scanning procedure, The work station 204 may also operate to receive signals from the detector 210 for generating images resulting from the scanning procedures.

In addition, to further enhance the degrees of freedom provided by the system 200, the wall stand 208 may include a laterally projecting member 218 mounted on a vertical column 220. The laterally projecting member 218 may be vertically moveable and/or adjustable and may be fixed at any suitable height to provide a proper image of the desired area of the patient 205. A distal end of the laterally projecting member 218 may include a tiltable bucky 222 for holding the detector 210.

However, though the positioning of the X-ray source 110, 214 is adaptable using either the overhead tube support system 100 or the robotic arm 202 and the adjustment capabilities of the table 206 and wall stand 208 employed therewith to position the detector 210, the ability of the system 100, 200 to obtain the desired images of patients 205 in many situations is still limited by the construction of the system 100, 200.

In particular, one shortcoming of these imaging systems 100,200 is that in emergency or trauma situations it is often not convenient to reposition the patient 205 on the table 206 and/or in front of the wall stand 208. As a result, it is difficult for the typical positioning system 100, 200 to complete the required imaging examination without moving the patient 205 in order to obtain the desired images of the patient 205.

Further, in many situations there is a need to perform a 3D imaging examination when the patient 205 is in a standing position in order to see the details of the natural joint or spine, e.g., for certain clinical requirements. However, the standing position of the patient 205 cannot be accommodated by classical 3D imaging processes/systems, such as computed tomography (CT) or magnetic resonance imaging (MRI) systems, which require the patient 205 to lie on the patient support/table 206, thereby preventing a complete 3D scanning field for the system around the patient 205. In particular, current tomosynthesis utilizing a general radiographic device, i.e., X-ray source 110,214 cannot obtain a clear image due to the limited shot and scan angle, which is usually less than 45°. For a complete tomographic scan it is desired to be able to have a scan angle of 180° or more.

In addition, under some circumstances, it is required to control the positioning of the X-ray system 100,200 from a separated control room when it is necessary to isolate the patient from operator to avoid potential infection. However, while the X-ray source 110, 214 can be moved from the control room, when the patient 205 is disposed on the table 206, the operator is still required to move the table top to locate the field of view (FOV) of the X-ray source 110,214 over the desired area or field of interest (FOI) of the patient 204 to be imaged.

In one development with regard to these shortcomings, certain X-ray systems have been developed that include two ceiling suspension systems, one for supporting and moving the X-ray source and the other for supporting and moving the detector. However, these systems have significant increases to be both cost and complexity, making a two ceiling suspension system no practical for many environments.

Therefore, it is desirable to develop an improved system and method for positioning an X-ray source and a X-ray detector relative to a patient that overcomes these limitations of the prior art.

SUMMARY OF THE DISCLOSURE

According to one aspect of an exemplary embodiment of the disclosure, an X-ray system with a universal positioning system includes a multiple degree of freedom overhead support system adapted to be mounted to a surface within a location for the X-ray system, a first imaging device mounted on the overhead support system, a multiple degree of freedom wall stand disposed within the location for the X-ray system, the wall stand comprising a motive module and a number of rotatable members operably connected to the motive module that can be rotated by the motive module to move the wall stand over a floor of the location, a second imaging device mounted to the wall stand, a table disposed within the location for the X-ray system, the table comprising a base disposed on the floor of the location and a support surface secured at one end to the base, and a workstation including a processing unit configured to send control signals to and to receive data signals from the overhead support system, the first imaging device, the wall stand, the second imaging device and the table.

According to still another aspect of an exemplary embodiment of the disclosure, method of X-ray imaging includes the steps of providing an X-ray imaging system with a universal positioning system having a multiple degree of freedom overhead support system adapted to be mounted to a surface within a location for the X-ray system, a first imaging device mounted on the overhead support system, a multiple degree of freedom wall stand disposed within the location for the X-ray system, the wall stand comprising a motive module and a number of rotatable members operably connected to the motive module that can be rotated by the motive module to move the wall stand over a floor of the location, a second imaging device mounted to the wall stand, a table disposed within the location for the X-ray system, the table comprising a base disposed on the floor of the location and a support surface secured to the base at one end, a track disposed on the floor of the location and on which the wall stand is disposed, and a workstation including a processing unit configured to send control signals to and to receive data signals from the overhead support system, the first imaging device, the wall stand, the second imaging device and the table, positioning a patient adjacent the track, moving the first imaging device into a location adjacent the patient, moving the second imaging device into a location adjacent the patient, where the second imaging device is positioned opposite the first imaging device relative to the patient, and performing an X-ray imaging procedure to obtain X-ray images of the patient.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. As used herein, the terms "substantially," "generally," and "about" indicate conditions within reasonably achievable manufacturing and assembly tolerances, relative to ideal desired conditions suitable for achieving the functional purpose of a component or assembly. Also, as used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process.

Figure 1:
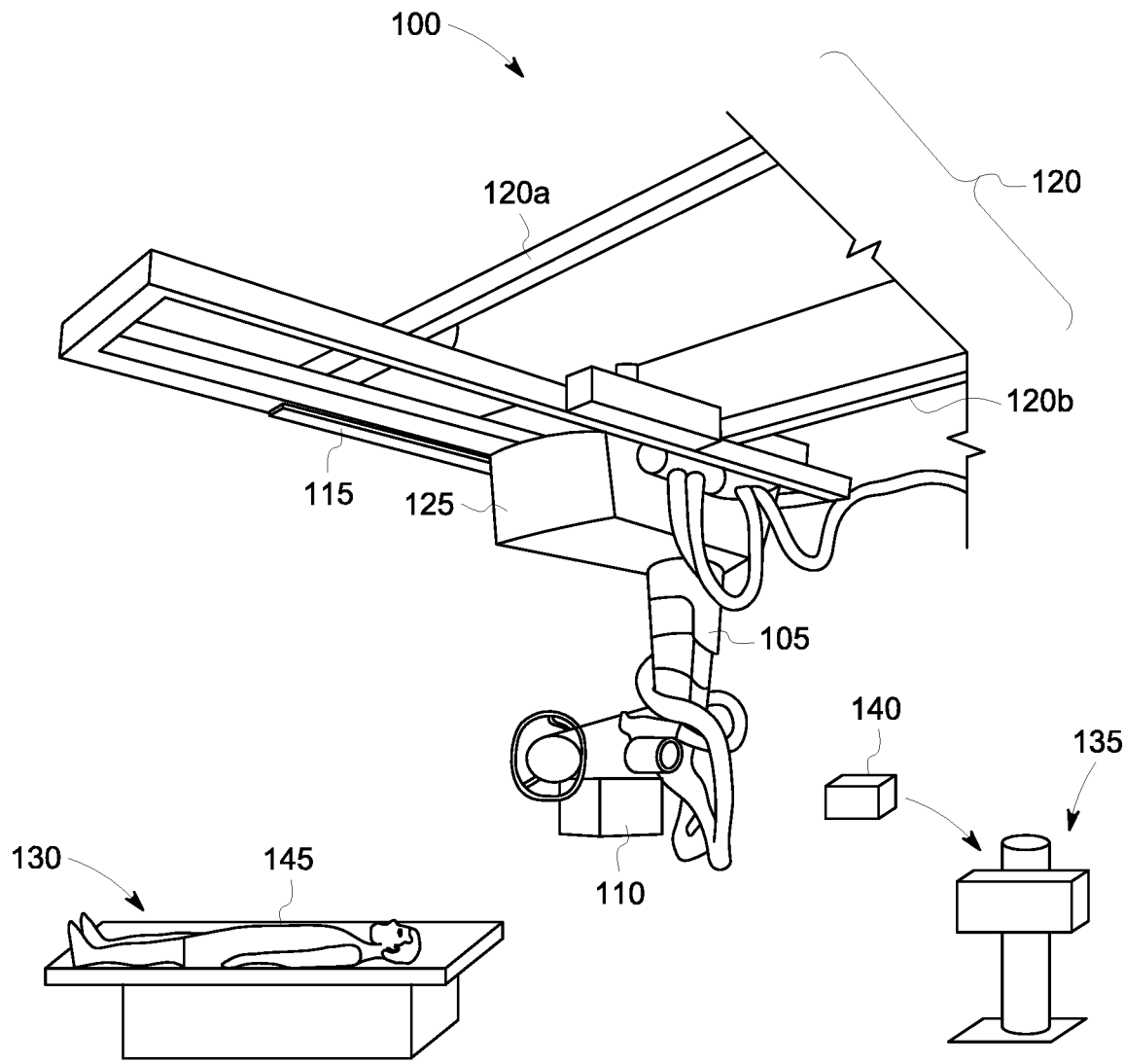
FIG. 1 shows a diagram of a prior art imaging system utilizing an overhead tube support system.
Figure 2:
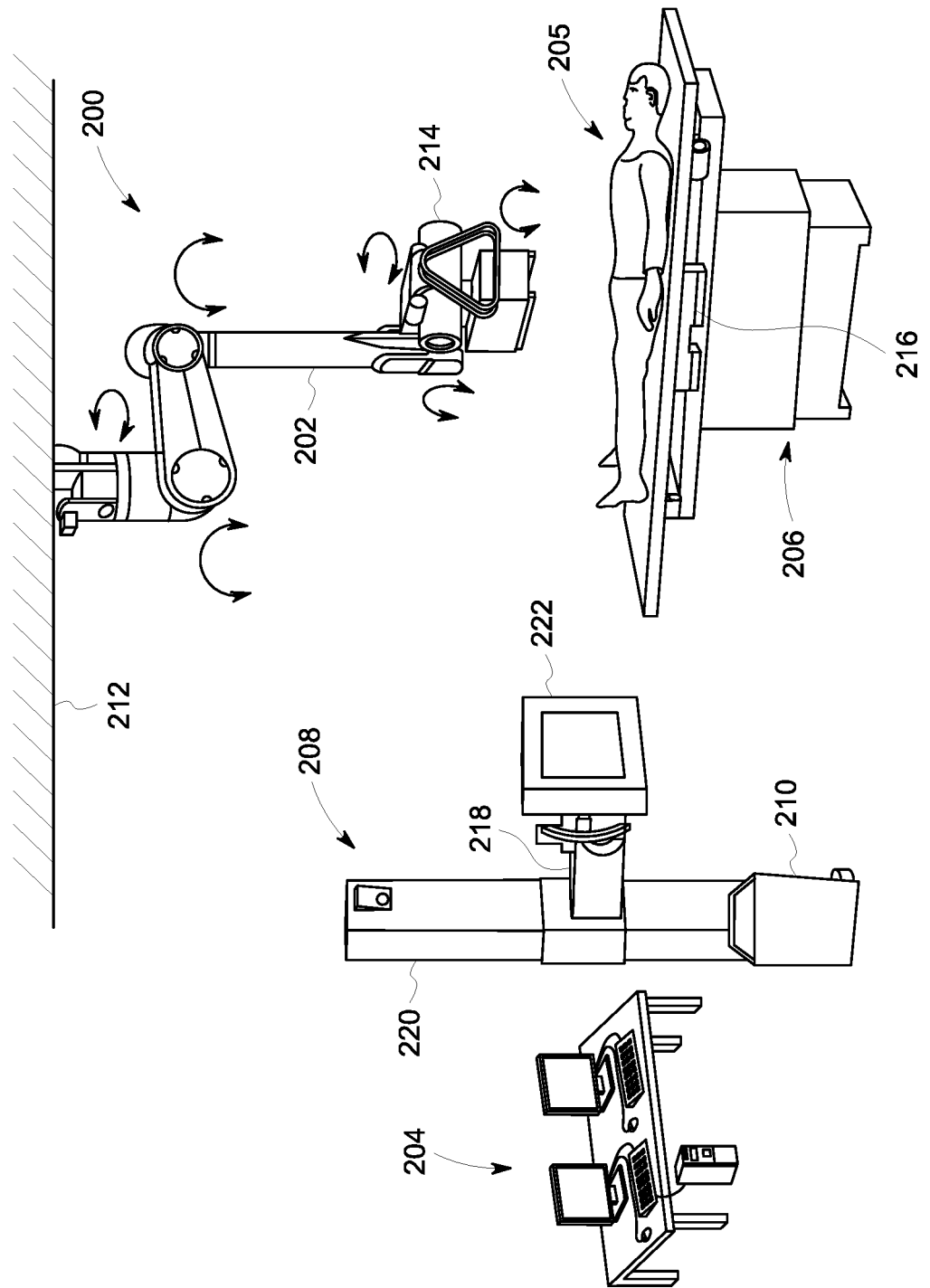
FIG. 2 shows a diagram of a prior art imaging system utilizing a robotic arm tube support system.
Figure 3:
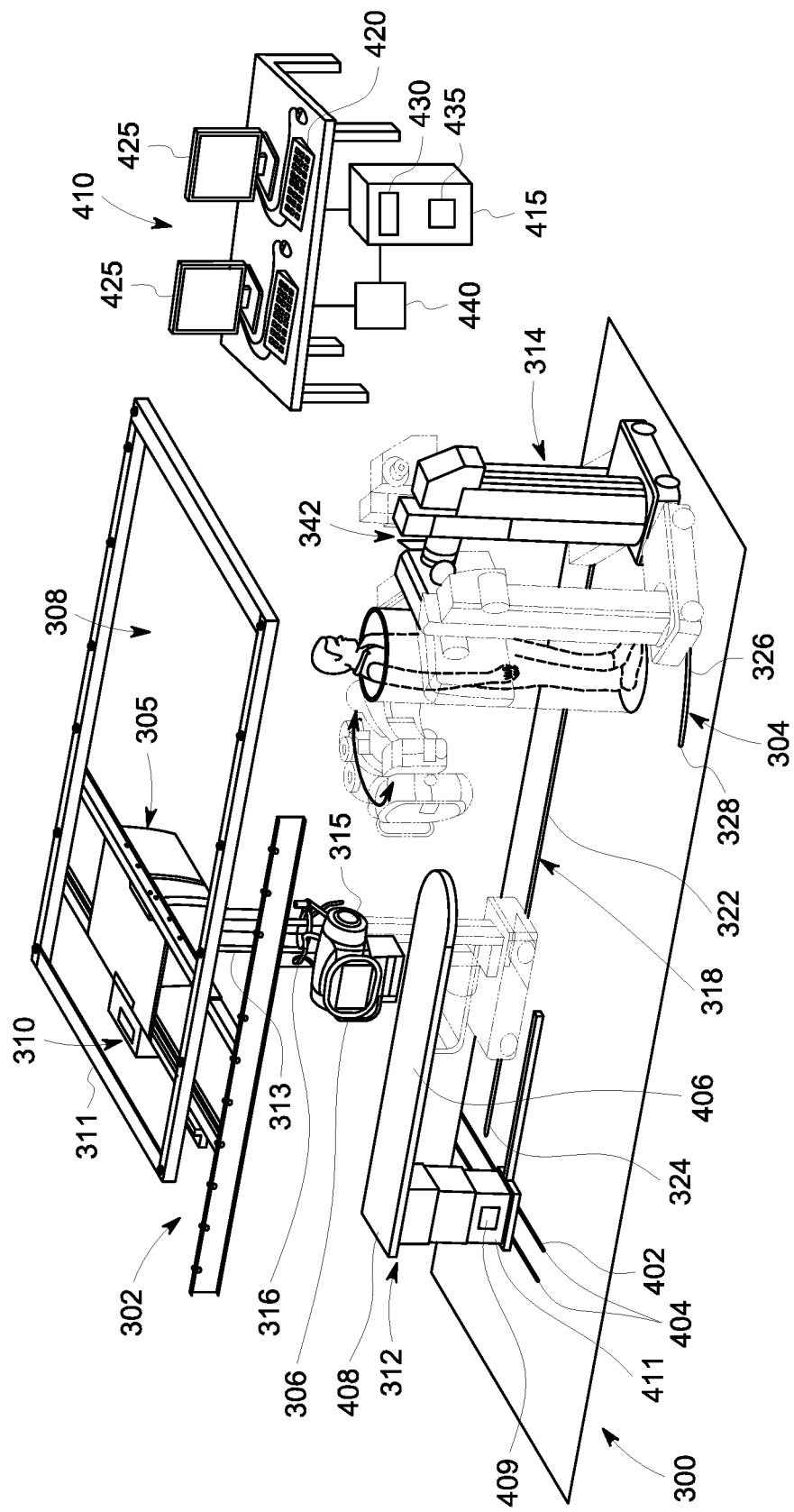
FIG. 3 is an isometric view of a radiography suite including an imaging system with the universal positioning system according to an exemplary embodiment of the disclosure.

FIG. 3 shows an exemplary embodiment of a radiography suite 300 including a fixed X-ray system 302 having a universal positioning system 304 according to the disclosed embodiments. The X-ray system 302 includes a suitable control subsystem (not shown) disposed on a workstation 410 for controlling the movement and operation of the various components of the X-ray system 302.

The X-ray system 302 is formed with a first imaging device 306, which can be either an X-ray tube or a detector, that is secured by a moveable mount 305 to a portion of the suite 300 or other location in which the X-ray system 302 is disposed, such as a wall or ceiling 308 of the suite 300, where the moveable mount can be an overhead support system 310 or a robotic arm, a table 312, a wall stand 314, and a second imaging device 342, which can be the other of the X-ray tube or the detector forming the first imaging device 306. The overhead support system 310 provides five (5) separate degrees of freedom/axes of automated or manually-directed movement for the first imaging device 306, and in particular allows for lateral and longitudinal movement along a suspended track 311 for the overhead support system 310, vertical movement via a telescopic column 313 attached to and moveable along the suspended track 311, rotational movement relative to the column 313 provided by the rotation of the column 313, and angular movement provided by a pivot mechanism 315 disposed between the column 313 and the first imaging device 306. The overhead support system 310 also includes a suitable position monitor 316 in order to provide accurate and precise location information regarding the position of the first imaging device 306 disposed on the overhead support system 310.

It should also be understood that the fixed X-ray system 302 may also include other components suitable for implementing the disclosed embodiments. The term radiography suite generally refers to a room or rooms which are configured for performing radiography procedures typically using X-ray imaging techniques. Exemplary radiography procedures may include but are not limited to Computed Tomography (CT), computerized axial tomography (CAT) scanning, and fluoroscopy.

Looking now at FIGS. 3-6, the universal positioning system 304 includes a track 318 disposed on the floor 100 of the suite 300. The track 318 can be formed as desired, and in the illustrated exemplary embodiment includes a straight section 322 extending from one end 324 of the track 318 to a curved section 326 that terminates at the opposite end 328 of the track 318. The curved section 326 of the track 318 traverses an arc of at least 180° between the straight section 322 and the second end 328, though any larger or smaller length arc for the curved section 326 is also contemplated as being within the scope of the disclosure, along with any other combination or arrangement of straight sections 322 and/or curved sections 326, as desired. On the track 318 is disposed the wall stand 314, such that the wall stand 314 can move along the track 318 between the opposed ends 324, 328 of the track 318.

Figure 4:
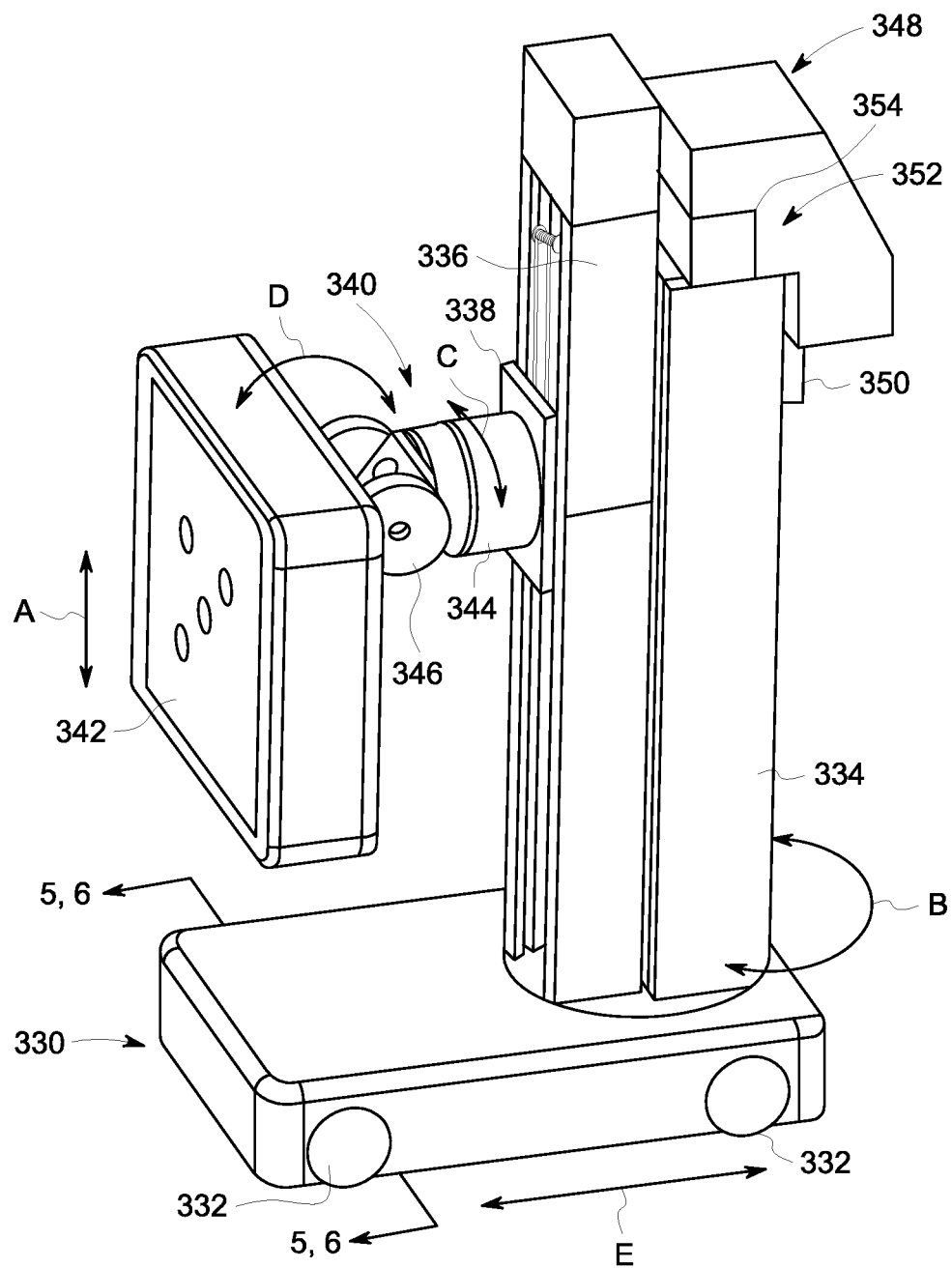
FIG. 4 is an isometric view of a wall stand utilized with the imaging system and universal positioning system of FIG. 3.

In the illustrated exemplary, embodiment shown in FIG. 4, the wall stand 314 includes moveable base 330 having a number of support wheels or casters 332 thereon, a fixed column 334 extending upwardly from the base 330, a movable or extendable column 336 attached to the fixed column 334 and a carriage 338 disposed on the moveable column 336 opposite the fixed column 334. The carriage 338 includes a support arm 340 extending outwardly from the carriage 338 opposite the moveable column 336, where the arm 340 supports a second imaging device 342 opposite the carriage 338. The support arm 340 includes a rotational module 344 adjacent the carriage 338 and a tilting module 346 between the rotational module 344 and the second imaging device 342.

The wall stand 314 provides five (5) degrees of freedom/axes of movement for the second imaging device 342 as shown in FIG. 4. First, the second imaging device 342 can move in a vertical direction indicated by arrow A due to the movement of one or both of the moveable column 336 with regard to the fixed column 334, or the movement of the carriage 338 with regard to the moveable column 336. Second, the second imaging device 342 can move in a rotational direction indicated by arrow B around a vertical axis by the rotation of the fixed column 334 relative to the base 330. Third, the second imaging device 342 can rotate around a first horizontal axis in a direction indicated by arrow C due to the operation of the rotational module 344 of the support arm 340. Fourth, the second imaging device 342 can tilt around a second horizontal axis perpendicular to the first horizontal axis in the direction indicated by arrow D due to the operation of the tilting module 346 of the support arm 340. Fifth, the second imaging device 342 can move in a horizontal direction indicated by arrow E due to the movement of the base 330.

To control the positioning of the second imaging device 342 relative to the wall stand 314, the wall stand 314 includes a control device 348 disposed thereon. In some embodiments, the control device 348 includes a control circuit board 350 for receiving wired or wireless control signals sent by the workstation 410 of the X-ray imaging system 302 and controlling the corresponding components or modules in the wall stand 314. Specifically, the control device 348 may receive a control signal to enable the control device 348 to operate a driving module 352 on the wall stand 314, where the driving module 352 is formed of a motor 354 operably connected to the various moveable components of the wall stand 314. For example, when a control signal received by the control device 348 includes the height and angle of the second imaging device 342 required for a current scan, the control device 348 can operate the motor 352 to position the second imaging device 342 at a preset height and rotational angles through the movement of the different components of the wall stand 314. The control device 348 can additionally supply accurate and precise position data regarding the location of the second imaging device 342 as positioned by the operation of the control device 348.

Figure 5:
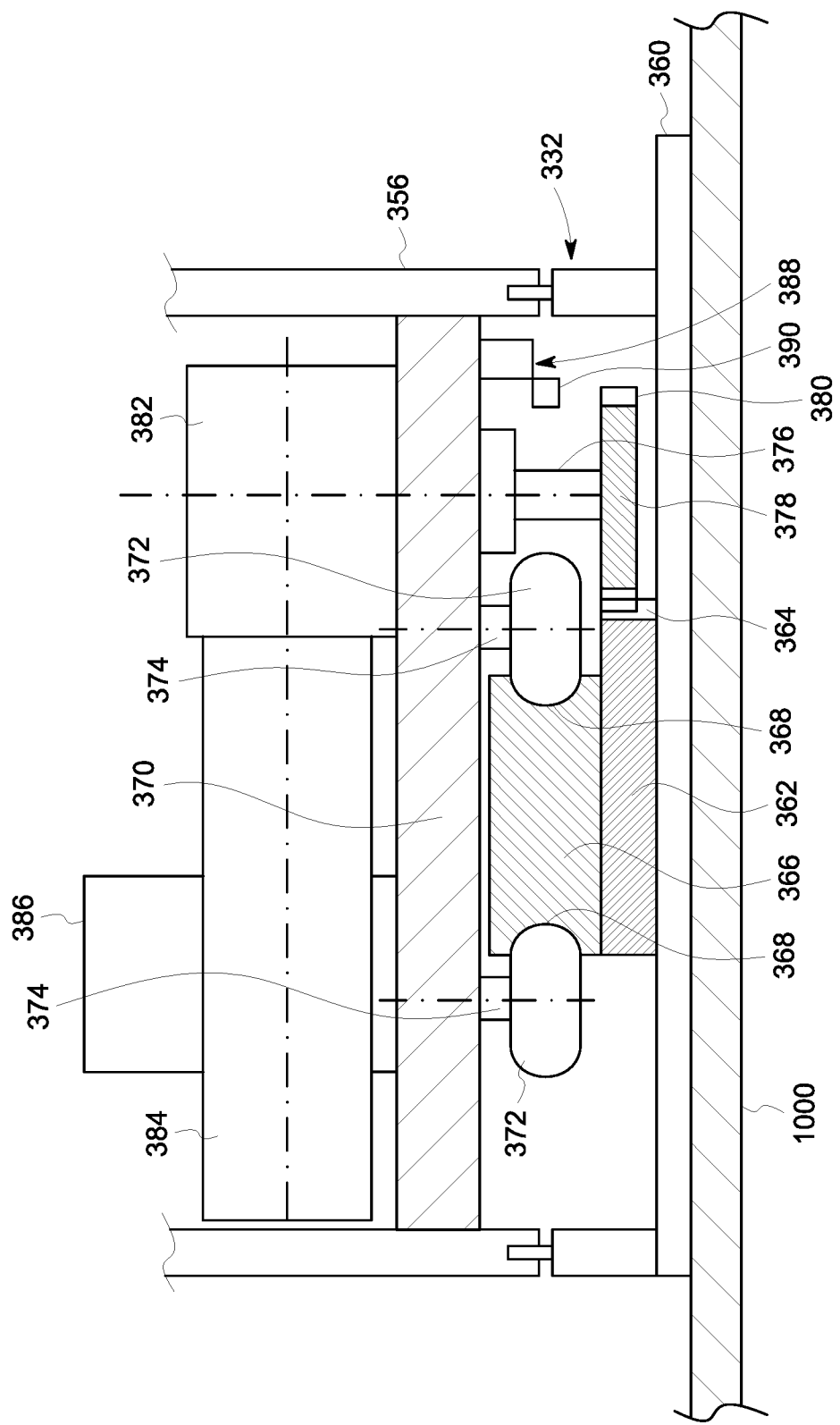
FIG. 5 is a partially broken away, cross sectional view along line 5-5 of FIG. 4.
Figure 6:
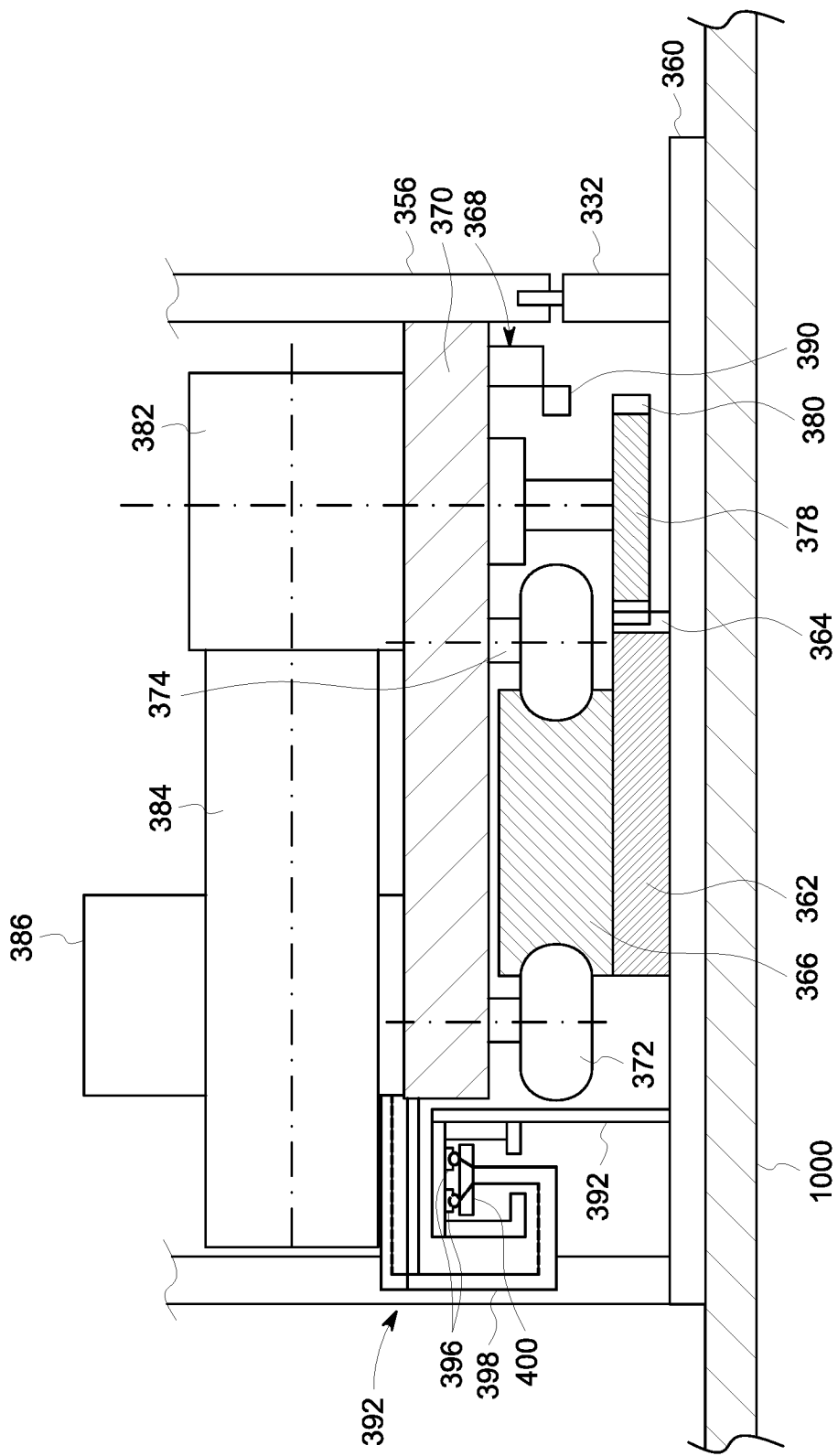
FIG. 6 is a partially broken away, cross sectional view similar to FIG. 5 showing an alternative exemplary embodiment of the wall stand.

Referring now to FIGS. 5 and 6, the base 330 of the wall stand 314 is disposed directly over the track 318 in order to enable the track 318 to guide the movement of the base 330 and thus the wall stand 314 along the track 318. In one exemplary embodiment for the base 330, the base 330 includes a housing 356 to which the wheels 332 are rotatably secured in any suitable manner to enable the wheels 332 to rotate freely with regard to the housing 356 while supporting the weight of the base 330 and remainder of the wall stand 314. Within the housing 356, the base 330 encloses a motive module 358 engaged with and operable to move the base 330 along the track 318.

In the exemplary illustrated embodiment of FIG. 5, the track 318 is formed with a base plate 360 secured to the floor 1000 of the suite 300. The base plate 360 is fixed on the floor 1000 by suitable anchors (not shown) to prevent movement of the base plate 360 relative to the floor 1000. The base plate 360 can be formed to have a width that is sufficient for the casters 332 on the base 330 to be supported on the base plate 360 or on a dedicated support surface (not shown) which is fixed relative to the base plate 360 in order to maintain the alignment of the wall stand 314 with regard to the base plate 360 and the track 318.

The base plate 360 also supports a gear rack 362 opposite the floor 1000. The rack 362 includes a number of evenly spaced teeth 364 located along one side of the rack 362 and supports a guide rail 366 opposite the base plate 360. The guide rail 366 includes a pair of engagement surfaces 368 located on opposite sides of the guide rail 366.

To engage the track 318, the motive module 358 has a frame member 370 disposed above the guide rail 366 and forming a part of the housing 356 for the base 330. The frame member 370 is positioned above the guide rail 366 by one or more stabilizing members 371 formed in the illustrated exemplary embodiment as a pair of rollers 372 engaged with the engagement surfaces 368 on each side of the guide rail 366 and connected to the frame member 370 by shafts 374 extending between the rollers 372 and the frame member 370. The rollers 372 are fixed to the frame member 370 by the shafts 374 but can rotate freely on the shafts 374, such that the rollers 372 can move along the engagement surfaces 368 while maintaining the frame member 370 in a stable position above the guide rail 366.

The frame member 370 also includes a drive shaft 376 extending outwardly from the frame member 370. The drive shaft 376 is spaced from the roller shaft 374 and includes a rotatable member or pinion/gear 378 disposed opposite the frame member 370. The gear 378 includes a number of peripheral teeth 380 that mesh with the teeth 364 on the gear rack 362. The drive shaft 378 is operably connected to a gearbox or transmission 382 supported on the frame member 370 that in turn is operably connected to a motor 384. The motor 384 is powered in any suitable manner, such as by a rechargeable battery 386 disposed within the housing 356 on the frame member 370 and connected to the motor 384. Alternatively, the motor 384 can be powered by a direct power supply, such as by an electrical connection to the motor 384 using a cable chain or cable drape (not shown), that is connected to the wall stand 314 at one end, and along the overhead support system 310 to a power supply (not shown) at the opposite end, with a guide device (not shown) for the cable chain or drape fixed in parallel to the track 318 to control the movement of the cable chain or drape in conjunction with the movement of the wall stand 314 along the track 318.

The operation of the motor 384 is controlled by the control device 348, which is operably connected to the motor 384. Thus, when the drive shaft 376 is rotated by the operation of the motor 384 under the control of the control device 348, the gear 378 rotates and the engagement of the teeth 380 on the gear 378 with the teeth 364 on the rack 362 causes the rollers 372 to move along the engagement surfaces 368 of the guide rail 366. The movement of the frame member 370 In this manner the frame member 370 and housing 356 are moved along the track 318 in a closely controlled manner to ensure accurate positioning of the base 330 and wall stand 314 where desired.

To track the exact positioning of the base 330 along the track 318, the frame member 370 also supports a position detector 388 thereon. The position detector 388 is capable of determining the exact position of the base 330 and thus the wall stand 314 along the track 318, to enable exact positioning of the second imaging device 342 during an imaging procedure. In one embodiment, the position detector 388 can take the form of another pinion gear (not shown) connected with an encoder shaft (not shown) or a potential meter shaft (not shown) and engaged with the rack 362 to provide data on the position of the motive module 358 relative to the track 318 based on the sensed rotation of the encoder/potentiometer shaft. In an alternative exemplary embodiment, illustrated in FIG. 5, the position detector 388 is formed with a sensor 390 that obtains position data from an interaction with the track 318. The sensor 390 can be a magnetic sensor, a camera, a laser sensor or a radar sensor, and can detect a magnetic signal from the track 318, can view position indications present on the track 318, or can detect the position of the motive module 358/base 330/wall stand 314 relative to the track 318 or other landmarks within the suite 300 using laser or radar positioning data.

In the embodiments where the power supply for the motor 384 is provided by the battery 386 disposed within the housing 356 of the base 330, to recharge the battery 386, the battery 386 can be removed and replaced, or charged in position within the housing 356, such as by plugging a suitable power source (not shown) into a receptacle (not shown) for the battery 386. Looking now at the illustrated exemplary embodiment of FIG. 6, in an alternative manner to recharge the battery 386 within the housing 356, a number of docking stations or points 392 are disposed along the track 318. For example, two docking point 392 for battery charging can be employed with one at or near each end 324,328 of the track 318. The docking station 392 includes a stationery conductor rail 394 fixed on the floor 1000 adjacent and parallel to the track 318. The conductor rail 394 is connected to a power supply (not shown) an includes a pair of contacts 396 disposed on the rail 394. A slip conductor carriage 398 is secured to the frame member 370 and includes a plate 400 located opposite the frame member 370 and positionable in engagement with the contacts 396. The slip conductor carriage 398 is operably connected to the battery 386, such that when the plate 400 makes contact with the contacts 396, power flows from the conductor rail 394 through the slip conductor carriage 398 to the battery 386. While the conductor rail 394 is disposed adjacent each end 324,328 of the track 318, in an alternative embodiment, the conductor rail 394 can extend over a longer portion of the track 318 or along the entire track 318, to ensure a more constant supply of power to the battery 386. In an alternative embodiment, the motive module 358 can omit the battery 386, with power being supplied directly to the second imaging device 342 and the motor 384 via a continuous power supply through the connection to the conductor rail 394 via the carriage 398. In addition, control signals for the control device 348, motive module 358, and/or the second imaging device 342 can be sent along the conductor rail 394, which can be formed separately from, or as a part of the track 318.

Referring now to FIG. 3, the table 312 is constructed to be motorized and capable of movement in any number of directions. The table 312 includes a base 402 attached to a one or more, and as illustrated in the exemplary embodiment of FIG. 3, a pair of rails 404 disposed on the floor 1000, and a support surface 406 mounted to the base 402 opposite the rails 404. The rails 404 can be formed with any suitable structure, such as a structure similar to that described previously for the track 318, and are positioned adjacent the track 318. In the illustrated exemplary embodiment, the rails 404 are oriented parallel to one another and are positioned with one rail 404 immediately adjacent the end 324 of the track 318 in an orientation perpendicular to the track 318. The connection of the base 402 to the rails 404 can be similar to that described for the attachment of the wall stand 314 to the track 318 in order to securely position the base 402 on the rails 404, but also can be any other suitable connection mechanism that enables the base 402 to move along the rails 404 in a secure and closely controllable manner.

Figure 10:
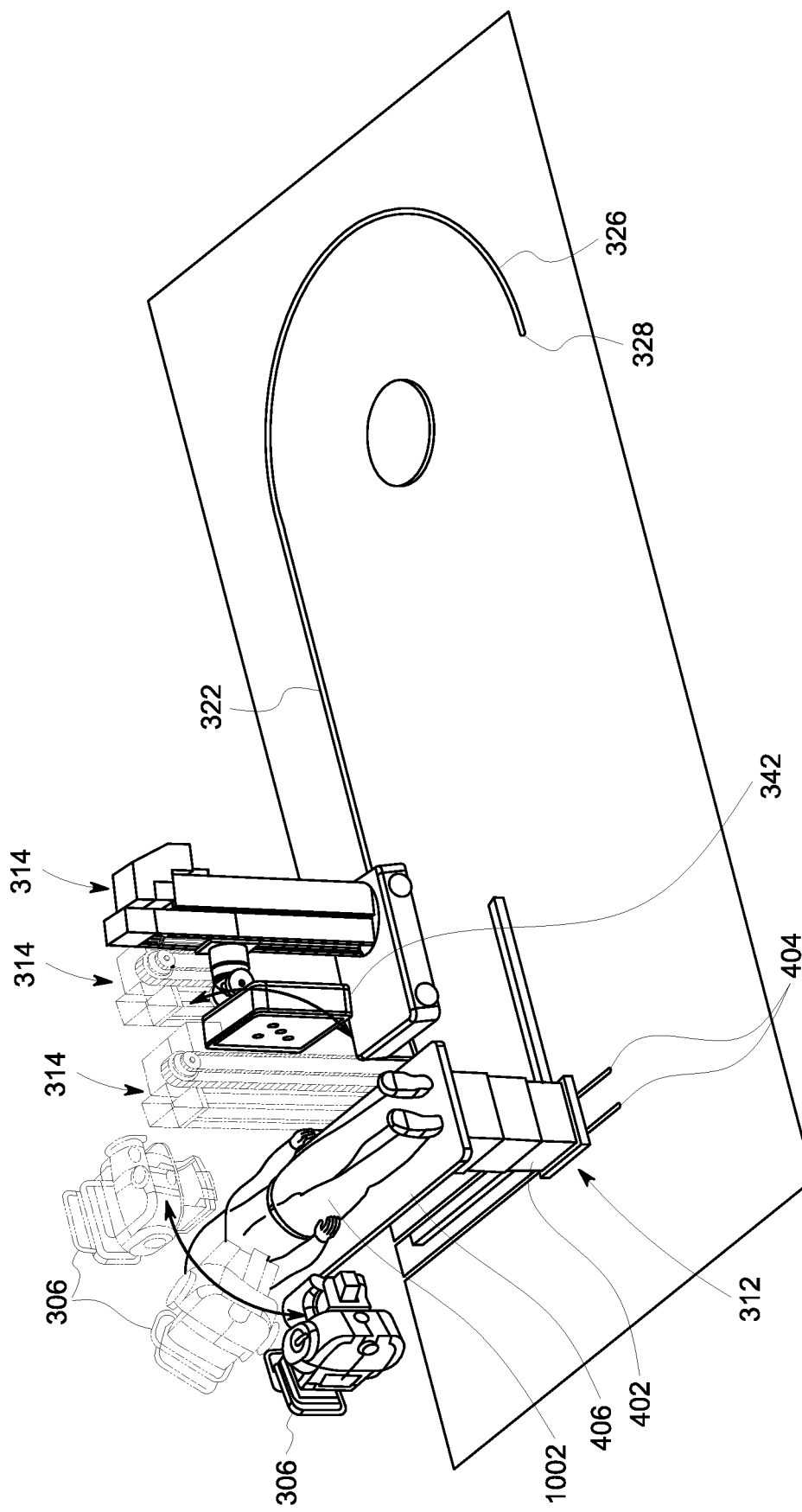
FIG. 10 is an isometric view of a radiography suite including an imaging system with the universal positioning system according to FIG. 3 in an alternative table 3D mode.

The base 402 can extend telescopically or in any other suitable manner to increase the height of the base 402 as desired, thereby raising the support surface 406 on which the patient 1002 can be positioned. Further, the support surface 406 is mounted at one end 408 to the base 402, such that the support surface 406 can be rotated relative to the base 402 between positions where the support surface 406 is oriented perpendicular to the rails 404 (FIG. 3) and where the support surface 406 is oriented parallel to the rails 404 (FIG. 10). Further, as the overhead support system 310 supports the first imaging device 306 and the wall stand 318 supports the second imaging device 342, the table 312 can be formed without any bucky or other suitable connection point for the placement of detector within the table 312, and more specifically within the support surface 406, thereby greatly simplifying the construction of the support surface 406.

The base 402 includes a motive mechanism 409 that enables the position of the base 402 and/or the support surface 406 relative to the base 402 to be controlled through signals sent to the motive mechanism 409. The motive mechanism 409 is also operable to move the base 402 along the rails 404. In this manner the height of the base 402, the position of the support surface 406 and the position of the base 402 along the rails 404 can be adjusted and/or controlled as necessary prior to and/or during an imaging procedure using the X-ray system 302. Further, in order to monitor the position of the base 402, and thus the support surface 406 and patient 1002, along the rails 404, the motive mechanism 409 can include a position detection mechanism 411 similar to the position detector 388 utilized with the wall stand 314 and track 318 to accurately determine the location of the base 402/support surface 406/patient 1002 disposed in a prone position on the support surface 406 along the rails 404.

Each of the overhead support system 310, the first imaging device 306, the wall stand 314, the second imaging device 342 and the table 312 are operably connected to a workstation 410 forming a part of the universal positioning system 304, which in an exemplary embodiment is disposed remotely from the X-ray system 302 and universal positioning system 304, such as at a location outside of the radiography suite 300. The workstation 410 may include a computer 415, one or more input devices 420, for example, a keyboard, mouse, or other suitable input apparatus, and one or more output devices 425, for example, display screens or other devices providing data from the workstation 410. The workstation 410 may receive commands, scanning parameters, and other data from an operator or from a memory 430 and processor 435 of the computer 415. The commands, scanning parameters, and other data may be used by the computer 415/processor 435 to exchange control signals, commands, and data with one or more of the overhead support system 310, the first imaging device 306, the table 312, the wall stand 314, and the second imaging device 342 through a suitable wired or wireless control interface 440 connected to each of these components of the fixed X-ray system 302. For example, the control interface 440 may provide control signals to and receive image, position or other data signals from one or more of the overhead support system 310, the first imaging device 306, the table 312, the wall stand 314, and the second imaging device 342.

The workstation 410 may control the frequency and amount of radiation produced by the X-ray source 306 or 342, the sensitivity of the detector 306 or 342, and the positions of the table 312 and wall stand 314 in order to facilitate scanning operations. Signals from the detector 306 or 342 may be sent to the workstation 410 for processing. The workstation 410 may include an image processing capability for processing the signals from the detector 306 or 342 to produce an output of real time 2D or 3D images for display on the one or more output devices 425. Further, with the 5 axes of motion provided by each of the overhead support system 310 and the wall stand 314, the universal positioning system 304 enables the X-ray system 302 to perform classical table imaging an wall stand procedures with only a single detector 306,342. In addition, the ability of the overhead support system 310, the table 312 and the wall stand 314 to be operated automatically provides an X-ray imaging system 302 utilizing the universal positioning system 304 with the ability for the X-ray imaging system 302 to be completely remotely controlled, such as via the workstation 410.

With the movement capabilities and accuracy provided by the universal positioning system 304, the X-ray system 302 can be positioned to obtain X-ray images in a variety of configurations using the first imaging device 306 and the second imaging device 342, as shown in FIGS. 7-11, in each of which the structure of the overhead support system 310 is removed for purposes of clarity.

Figure 7:
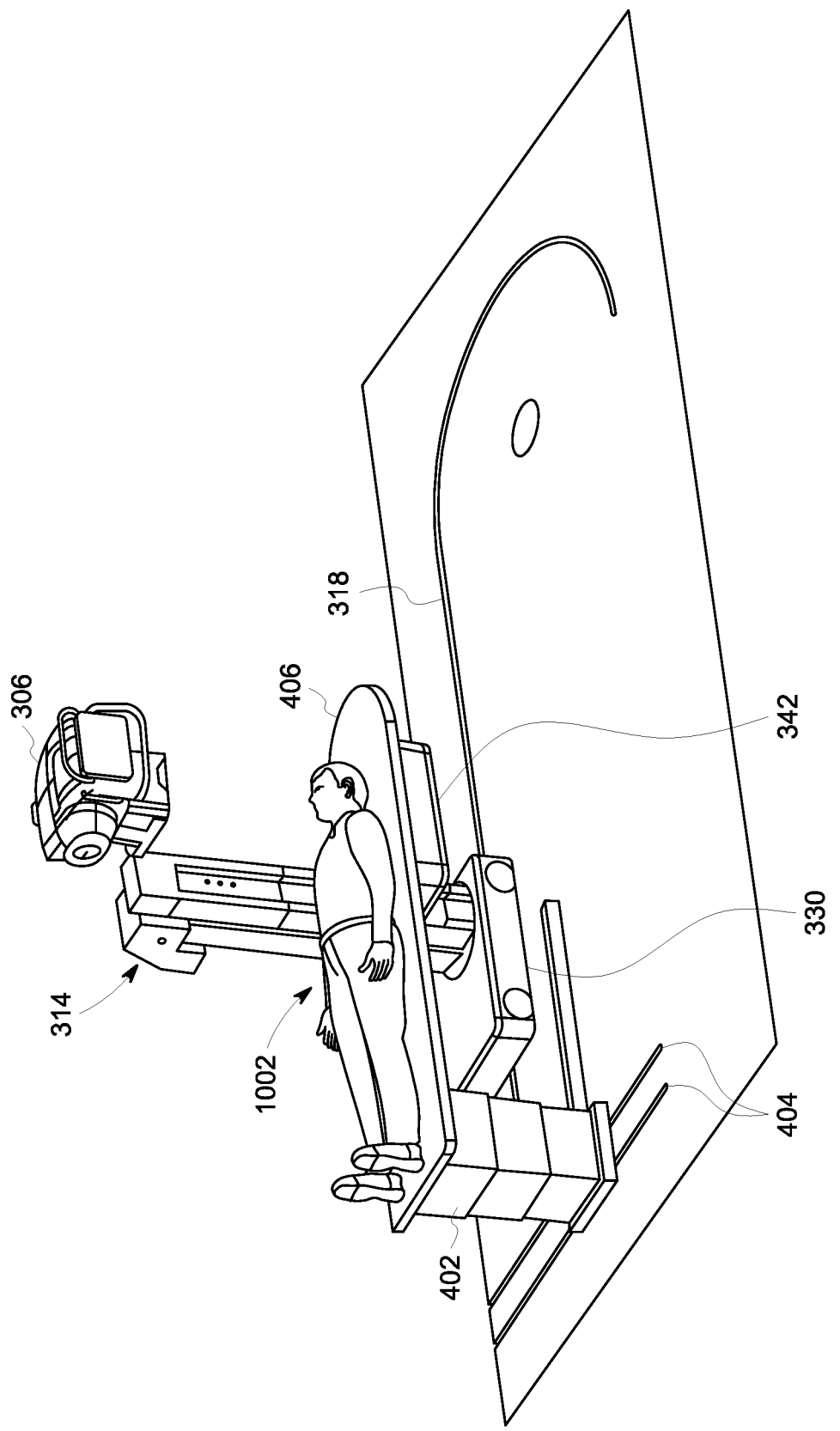
FIG. 7 is an isometric view of a radiography suite including an imaging system with the universal positioning system according to FIG. 3 in a table anterior/posterior (AP) mode.

Initially, as shown in FIG. 7, the universal positioning system 304 can be operated to dispose the table 312, the first imaging device 306 and the second imaging device 342 in a table anterior/posterior (AP) mode. As illustrated, the universal positioning system 304, as directed by automatic or manual control signals from the workstation 410, can move the wall stand 314 along the track 318 to position wall stand 314 in alignment with the support surface 406 of the table 312. Either during or after movement along the track 318, the wall stand 314 can rotate the fixed column 334 towards the support surface 406, lower the second imaging device 342 below the support surface 406 using one or both of the moveable column 336 and the carriage 338, and can rotate or tilt the second imaging device 342 into a parallel orientation with the support surface 406 using the rotational module 344 and/or the tilting module 346 of the support arm 340. The first imaging device 306 can be disposed in an aligned position with the second imaging device 342 using the overhead support system 310 and the positioning data provided to the workstation 410 regarding the exact location of the wall stand 314 and second imaging device 342 by the position detector 388 on the wall stand 314. From the initial position of the first imaging device 306 and the second imaging device 342 provided by the universal positioning system 304, the system 304 can operate the first and second devices 306,342 to obtain the desired image of the patient 1002. The system 304 can additionally traverse the wall stand 314 along the track 318 to other positions along the support surface 406, along with corresponding movements of the overhead support system 310, to position the first and second devices 306,342 in relation to other areas of the patient 1002 to be imaged.

Figure 8:
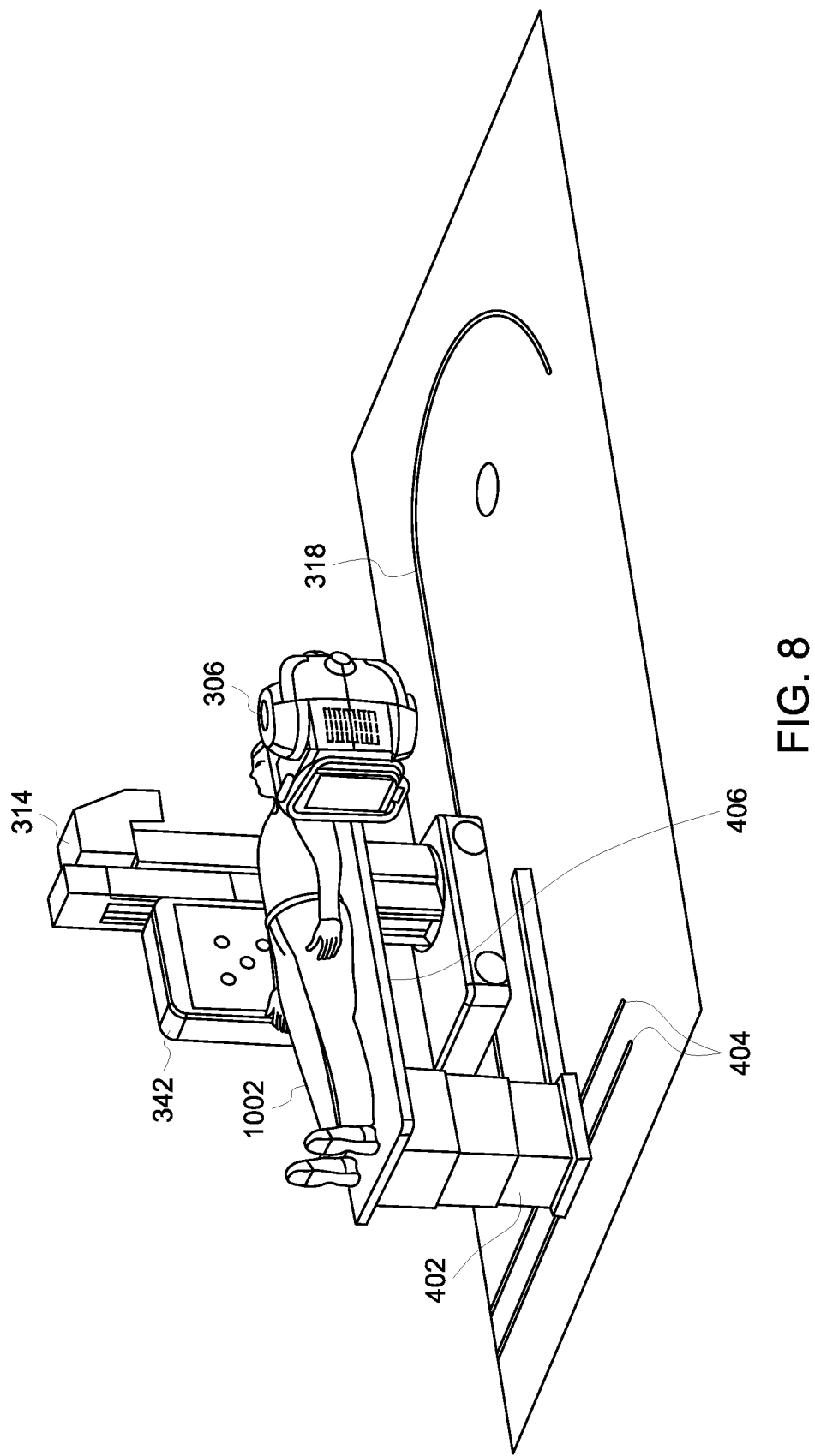
FIG. 8 is an isometric view of a radiography suite including an imaging system with the universal positioning system according to FIG. 3 in a table lateral mode.

Looking now at FIG. 8, the universal positioning system 304 can additionally enable the components of the X-ray imaging system 302 to operate in a lateral table mode. In particular, similar to the AP table mode, the universal positioning system 304 can move the wall stand 314 along the track 318 to position wall stand 314 in alignment with the support surface 406 of the table 312. Either during or after movement along the track 318, the wall stand 314 can raise or lower the second imaging device 342 into alignment with the patient 1002 on the support surface 406 using one or both of the moveable column 336 and the carriage 338, and can rotate or tilt the second imaging device 342 into a perpendicular orientation with the support surface 406 using the rotational module 344 and/or the tilting module 346 of the support arm 340. The first imaging device 306 can be aligned with the second imaging device 342 using the overhead support system 310 and the position information for the wall stand 314/second imaging device 342 in order to obtain the desired images of the patient 1002. The universal positioning system 304 can also move the wall stand 314/second imaging device 342 along the track 318 with corresponding movement of the first imaging device 306 using the overhead support system 310 to obtain additional images of the patient 1002.

Figure 9:
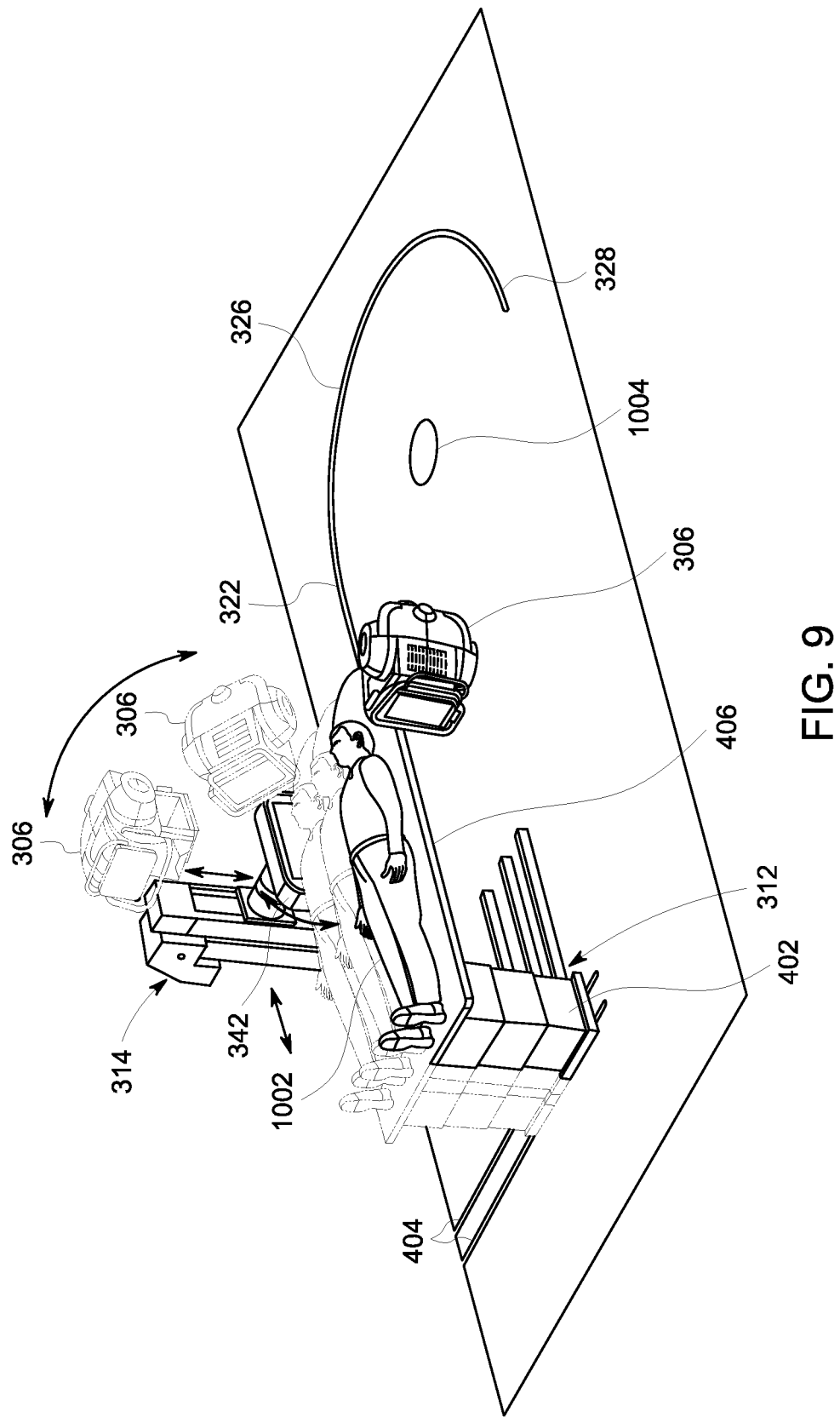
FIG. 9 is an isometric view of a radiography suite including an imaging system with the universal positioning system according to FIG. 3 in a table three-dimensional (3D) mode.

With capability of the universal positing system 304 for the first imaging device 306 and the second imaging device 342 to move in concert with one another around the support surface 406 under the direction of the workstation 410, the universal positioning system 304 enables the X-ray imaging system 302 to be operated to perform a 3D imaging or computed tomography procedure. As shown in FIG. 9, initially the universal positioning system 304 can move the wall stand 314 along the track 318 to locate the wall stand 314 and second imaging device 342 in alignment with the patient 1002 on the support surface 406. The second imaging device 342 can then be located in position directly below the patient 1002 on the support surface 406, with the first imaging device 306 moved into alignment with the second imaging device 342, similarly to the manner utilized for the table AP mode in FIG. 7. Upon initiation of the 3D imaging procedure, the workstation 410 can move the second imaging device 342 in an arc around the patient 1002 on the support surface 406 from below the patient 1002 to above the patient 1002, while moving the first imaging device 306 in a corresponding arc from above the patient 1002 to below the patient 1002, each in a continuous manner according to a set of step angles defined by a suitable tomography algorithm employed by/contained within the workstation 410. The first and second imaging devices 306,342 can be operated at any number of locations during the movement of the first and second imaging devices 306,342 in order to obtain the image data utilized by the workstation 410 to generate the 3D images of the selected areas of the patient 1002. Further, as illustrated in FIG. 9, in order to maintain the center of rotation of the arcs of the first and second imaging devices 306,342 on the desired area or field of interest (FOI) of the patient 1002, the universal positioning system 304 via the workstation 410 can move the base 402 of the table 312 along the rails 404 using the position data provided from one or both of the wall stand 314 and the overhead support system 310 regarding the position of the first and second imaging device 306,342. Additionally, to image different areas of the patient 1002 disposed in the support surface 406, the universal positioning system 304 can move the wall stand 314/second imaging device 342 along the track 318 into alignment with the selected area of the patient 1002, with a corresponding shift of the location of the overhead support system 310/first imaging device 306 to perform additional 3D scanning or imaging procedures.

As an alternative approach to the 3D imaging procedure illustrated in FIG. 9, in FIG. 10, the support surface 406 of the table 312 can be rotated over the base 402 into an orientation perpendicular to the track 318. The table 312 can move along the rails 404 to position the table 312 at a location where the entire field of interest (FOI) is positioned within the imaging scope defined by the universal positioning system 304. Once properly located, under the control of the workstation 410 to perform the 3D imaging/tomography, the wall stand 314 is moved along the track 318 to position the second imaging device 342 in alignment with the FOI of the patient 1002 on the support surface 406, while moving the first imaging device 306 utilizing the overhead support system 310 into a position opposed to the second imaging device 342. The wall stand 314 and the overhead support system 310 can rotate the first imaging device 306 and the second imaging device 342 around the center of the FOI in a manner similar to that used for the prior 3D imaging process in the embodiment of FIG. 9, but differing by maintaining the support surface 406 stationary and using the workstation 410 to control the multi-axis motion of longitudinal, vertical and tube angulation of the first imaging device 306 using the overhead support system 310 and to control the tilting, vertical and travel motion of the second imaging device 342 along the track 318 using the wall stand 314.

Figure 11:
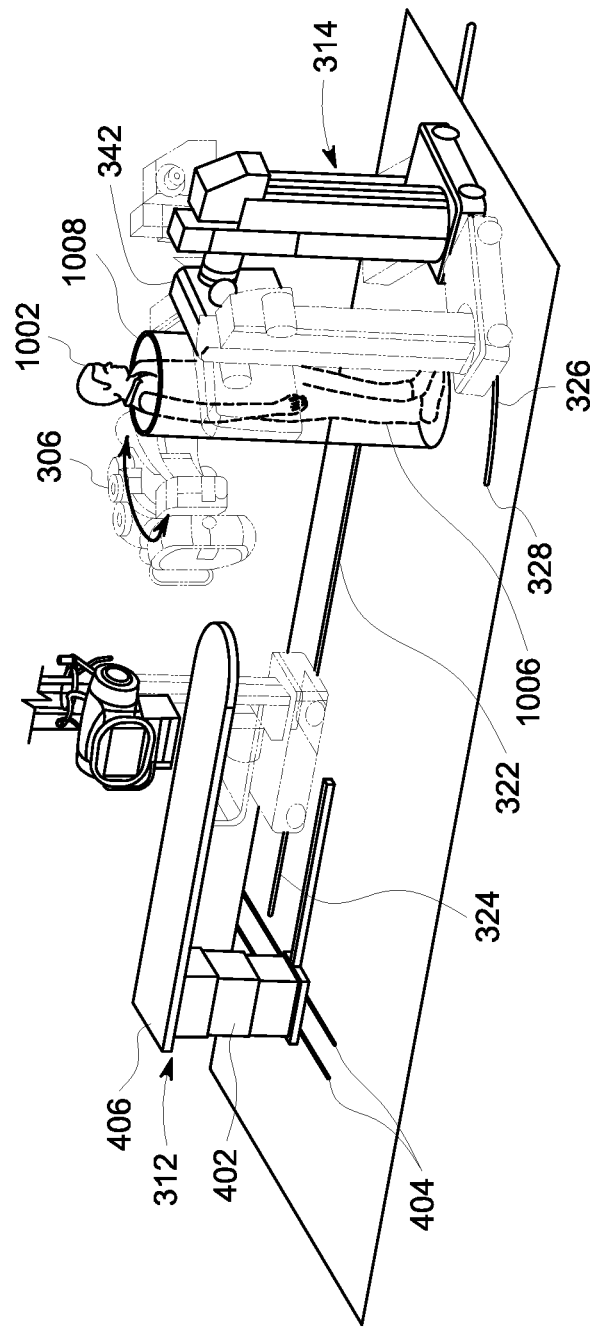
FIG. 11 is an isometric view of a radiography suite including an imaging system with the universal positioning system according to FIG. 3 in wall stand 3D mode.

In still another embodiment of the use of the universal positioning system 304 to perform imaging procedures with the X-ray imaging system 302, referring now to FIG. 11, the wall stand 314 can be moved along the track 318 onto the curved section 326. In this location for the wall stand 314, the patient 1002 can be located in a standing or upright position adjacent the wall stand 314 in order to image the patient 1002 in this upright position. The second imaging device 342 can be moved on the wall stand 314 in the previously described manners in order to position the second imaging device 342 in alignment with the FOI of the patient 1002. The overhead support system 310 can also move the first imaging device 306 to locate the first imaging device 306 opposite the second imaging device 342 in order to perform an X-ray imaging scan/procedure on the FOI, such as an anterior/posterior imaging procedure or a lateral imaging procedure.

Also, in this configuration for the X-ray imaging system 302 in FIG. 11 as enabled by the universal positioning system 304, when the patient 1002 is disposed at a specified focal point 1004 equidistant from the entire curved portion 326, which in the illustrated exemplary embodiment is shaped as one half of a circle with the focal point 1004 located at the center of the half circle, the wall stand 314 can be moved under the control of the workstation 410 to move the wall stand 314 and second imaging device 342 around the entire arc of the curved section 326, with corresponding movement of the first imaging device 306 by the overhead support system 310 to enable a 3D X-ray imaging/tomographic procedure to be performed in the patient 1002 in the upright, standing position.

In either mode of operation of the X-ray imaging system 302 and the universal positioning system 304 in FIG. 11, to assist in supporting the patient in a stable, stationary position when performing the imaging procedure, in some embodiments a transparent plastic tube or barrier 1006 can be positioned around the patient 1002. The barrier 1006 is designed to support the patient 1002 with different support structures 1008, such as hand and/or jaw rest(s). In the embodiment where the barrier 1006 includes a jaw rest, the barrier 1006 enables the X-ray imaging system 302 with the universal positioning system 304 to be operated to provide dental images of the patient 1002, without the need for specialized dental imaging devices.

In still another exemplary embodiment of the disclosure, the universal positioning system 304 can employ omnidirectional wheels (not shown) as the rotatable members on the base 330 of the wall stand 314 that are connected to the motive module 358. The omnidirectional wheels would negate the need for the track 318, casters 332 and gear 378, and would allow for complete freedom of movement of the wall stand 314 over the floor 1000 within the radiography suite 300. With the position sensor 388 (radar, camera, laser, magnetic track sensor, etc.) disposed on the wall stand 314, and known positions of the table 312, and the patient 1002 on the support surface 406 of the table 312, the workstation 410 can operate the motive module 358 to turn the omnidirectional wheels in a manner to move the wall stand 314 into the desired location for performing an imaging procedure on the FOI of the patient 1002. As the omnidirectional wheels are normally shaped as spheres, they can adequately support the weight of the wall stand 314 as it is moved about the radiography suite 300.

In still a further exemplary embodiment of the disclosure, the track 318 can be formed with any desired number and configuration of straight sections 322 and curved sections 326. For example, the track 318 can include multiple straight sections 322 optionally interconnected with one another to accommodate multiple orientations of the wall stand 314 with regard to one or more tables 312 disposed within the radiography suite 300, along with one or more curved sections 326 connected to and/or interconnecting the straight sections 322 and defining one or more points 1004 for upright or standing imaging of a patient 1002.

With the use of the components of the universal positioning system 304 for the X-ray imaging system 302, it is also capable to obtain multiple types of images of a patient 1002 without having to move the patient 1002 into different locations or positions. More specifically, with the ability and degrees of movement of the first imaging device 306 using the overhead support system 310, the second imaging device 342 using the wall stand 314 and track 318, and the support surface 406 using the base 402 and rails 404, each of an anterior/posterior, a lateral and a 3D/tomographic imaging procedure can be performed on a patient 1002 lying prone on the support surface 406 without having to make the patient 1002 move relative to the support surface 406.

Finally, it is also to be understood that the systems 302,304 may include the necessary computer, electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor/processing unit/computer and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application(s)/algorithm(s) that adapts the computer/controller to perform the methods disclosed herein may be read into a main memory of the at least one processor from a computer-readable medium. The term "computer-readable medium", as used herein, refers to any medium that provides or participates in providing instructions to the at least one processor of the systems 302,304 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. An X-ray system with a universal positioning system comprising:
   - a multiple degree of freedom overhead support system adapted to be mounted to a surface within a location for the X-ray system;
   - a first imaging device mounted on the overhead support system;
   - a multiple degree of freedom wall stand disposed within the location for the X-ray system, the wall stand comprising a motive module and a number of moveable members operably connected to the motive module that can be operated by the motive module to move the wall stand over a floor of the location;
   - a second imaging device mounted to the wall stand;
   - a table disposed within the location for the X-ray system, the table comprising a base disposed on the floor of the location and a support surface secured at one end to the base;
   - a workstation including a processing unit configured to send control signals to and to receive data signals from the overhead support system, the first imaging device, the wall stand, the second imaging device and the table; and
   - a track disposed on the floor of the location and on which the wall stand is disposed,
   - wherein the track comprises:

one or more straight sections; and one or more curved sections defining a focal point equidistant from the one or more curved sections.

2. The X-ray system of claim 1, wherein the one or more curved sections are shaped as a half circle.

3. The X-ray system of claim 1, wherein the table is disposed adjacent one end of the track.

4. The X-ray system of claim 1, further comprising one or more rails disposed on the floor and to which the table is moveably mounted.

5. The X-ray system of claim 4, wherein the one or more rails are disposed perpendicular to the track.

6. The X-ray system of claim 1, wherein the support surface is rotatable with respect to the base.

7. The X-ray system of claim 3, wherein the motive module comprises:

a motor;

a drive shaft operably connected between the motor and the rotatable member; and a power source operably connected to the motor to supply power to the motor.

8. The X-ray system of claim 7, wherein the rotatable member is a drive gear and the track include a toothed rack engaged with the gear.

9. The X-ray system of claim 7, wherein the power source is operably connected to the track in order to receive power through the track.

10. The X-ray system of claim 8, wherein the power source is a rechargeable battery.

11. The X-ray system of claim 1, wherein the workstation is disposed in a location separate from the location of the X-ray system.

12. A method of X-ray imaging comprising:

providing an X-ray imaging system with a universal positioning system comprising:

a multiple degree of freedom overhead support system adapted to be mounted to a surface within a location for the X-ray system;

a first imaging device mounted on the overhead support system;

a multiple degree of freedom wall stand disposed within the location for the X-ray system, the wall stand comprising a motive module and a number of moveable members operably connected to the motive module that can be operated by the motive module to move the wall stand over a floor of the location;

a second imaging device mounted to the wall stand;

a table disposed within the location for the X-ray system, the table comprising a base disposed on the floor of the location and a support surface secured to the base at one end;

a track disposed on the floor of the location and on which the wall stand is disposed, the track including one or more curved sections defining a focal point equidistant from the one or more curved sections; and a workstation including a processing unit configured to send control signals to and to receive data signals from the overhead support system, the first imaging device, the wall stand, the second imaging device and the table;

positioning a patient adjacent the track;

moving the first imaging device into a location adjacent the patient;

moving the second imaging device into a location adjacent the patient, where the second imaging device is positioned opposite the first imaging device relative to the patient; and performing an X-ray imaging procedure to obtain X-ray images of the patient.

13. The method of X-ray imaging of claim 12, wherein the step of moving the second imaging device into a location adjacent the patient comprises moving the wall stand along the track.

14. The method of X-ray imaging of claim 12, wherein the step of positioning a patient adjacent the track comprises: placing the patient in a prone position on the table adjacent the track.

15. The method of X-ray imaging of claim 14, wherein the step of performing an X-ray imaging procedure comprises performing an anterior/posterior X-ray imaging procedure or a lateral X-ray imaging procedure.

16. The method of claim 14, wherein the table is movably mounted to one or more rails disposed on the floor, and wherein the step of performing an X-ray imaging procedure comprises performing an 3D X-ray imaging procedure.

17. The method of X-ray imaging of claim 12, wherein the step of positioning a patient adjacent the track comprises: placing the patient in a standing position adjacent the track.

18. The method of X-ray imaging of claim 17, wherein the step of performing an X-ray imaging procedure comprises performing an anterior/posterior X-ray imaging procedure, a lateral X-ray imaging procedure or a 3D X-ray imaging procedure.

* * * * *